(12) United States Patent
Sharp

(10) Patent No.: US 10,426,851 B1
(45) Date of Patent: Oct. 1, 2019

(54) PROTECTIVE STERILIZATION SYSTEM

(71) Applicant: Elizabeth Sharp, Plano, TX (US)

(72) Inventor: Elizabeth Sharp, Plano, TX (US)

( * ) Notice: Subject to any disclaimer, the term of this patent is extended or adjusted under 35 U.S.C. 154(b) by 0 days.

(21) Appl. No.: 15/436,830

(22) Filed: Feb. 19, 2017

Related U.S. Application Data

(60) Provisional application No. 62/297,307, filed on Feb. 19, 2016.

(51) Int. Cl.
*A61L 2/07* (2006.01)
*B65D 47/32* (2006.01)
*B65D 25/10* (2006.01)

(52) U.S. Cl.
CPC .............. *A61L 2/07* (2013.01); *B65D 25/10* (2013.01); *B65D 47/32* (2013.01)

(58) Field of Classification Search
CPC ........................................................ A61L 2/07
See application file for complete search history.

(56) References Cited

U.S. PATENT DOCUMENTS

| | | | | |
|---|---|---|---|---|
| 5,215,726 A | * | 6/1993 | Kudla | A61L 2/26 206/370 |
| 5,324,489 A | * | 6/1994 | Nichols | A61L 2/26 206/363 |

* cited by examiner

*Primary Examiner* — Donald R Spamer
(74) *Attorney, Agent, or Firm* — Eldredge Law Firm, LLC; Richard Eldredge

(57) ABSTRACT

A protective sterilization system that provides protection to implements for dental or surgical procedures while being sterilized and stored afterward. The system has a protective container that suspends the implement during this process to prevent it from being damaged by either the container or other implements. The container also serves to restrict contaminants from reaching the implements after sterilization.

3 Claims, 5 Drawing Sheets

PROTECTIVE STERILIZATION SYSTEM

BACKGROUND

1. Field of the Invention

The present invention relates generally to infection control systems, and more specifically, to a sterilization system for purifying objects used in environments were germs and other infectious agents are undesirable.

2. Description of Related Art

Sterilization systems are well known in the art and are effective means to remove germs and other infectious materials. For example, FIG. 1 depicts a conventional sterilization system 101 having a tray 103 that is holds tools 105, 107 while processed in an autoclave 109. During use, the tools 105, 107 are placed in the tray 103 which is then placed in the autoclave 109, where the implements 105, 107, are sanitized.

One of the problems commonly associated with system 101 is its limited use. For example, the tools 105, 107 can be damaged by collisions with other tools 105, 107 while being cleaned and transported in the tray 103. Additionally once the tools 105, 107 are removed from the autoclave 109 they are at risk of contamination.

Accordingly, although great strides have been made in the area of sterilization systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1A:
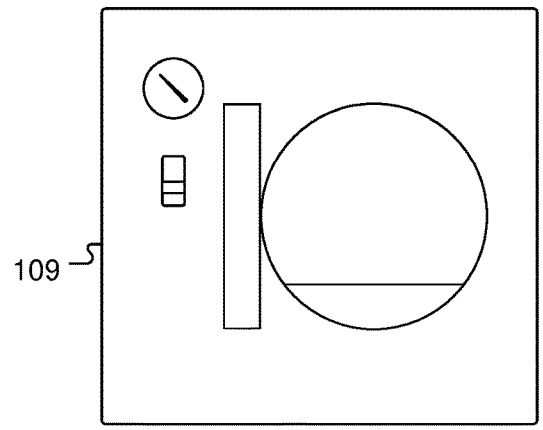
FIGS. 1A and 1B are front views of a common sterilization system.
Figure 1A:
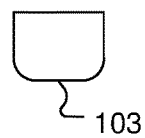
Figure 1B:
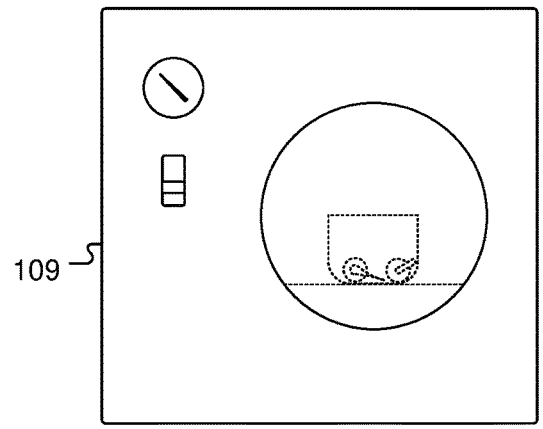

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional sterilization systems. Specifically, the system of the present application ensures that each implement is protected from damage while being cleaned and handled. In addition the tools are maintained in a sterile environment while being transported. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2A:
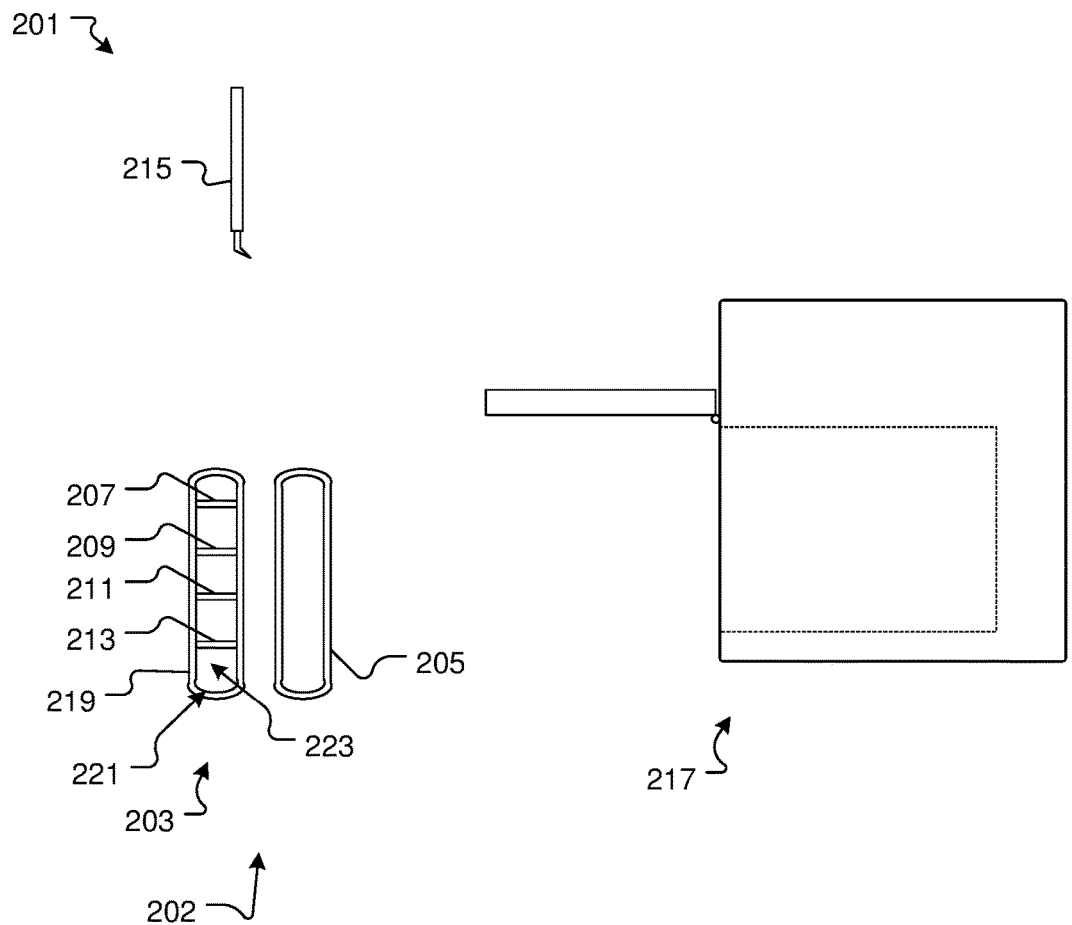
FIGS. 2A, 2B and 2C are top views of a protective sterilization system in accordance with a preferred embodiment of the present application.
Figure 2B:
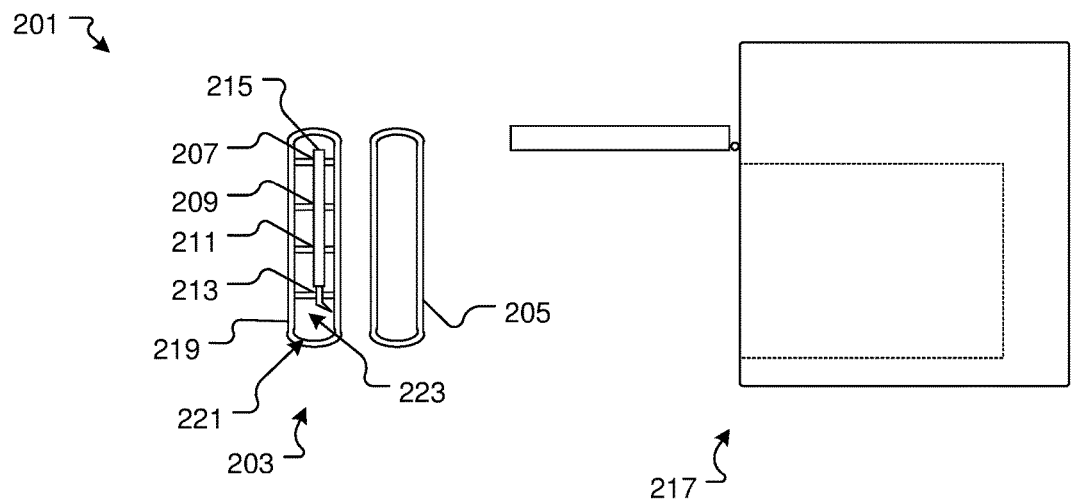
Figure 2C:
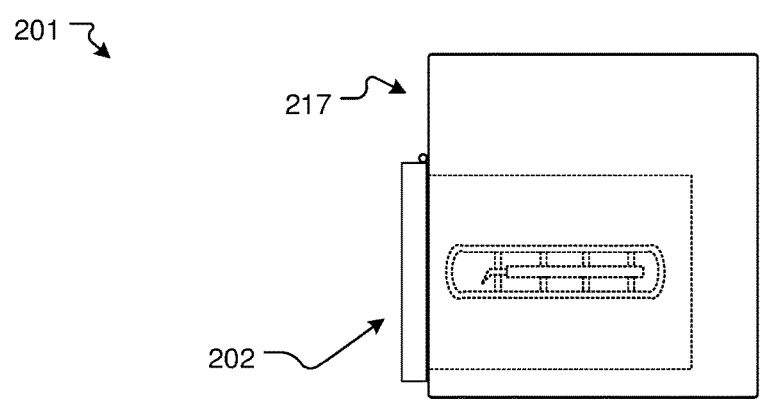

Referring now to the drawings wherein like reference characters identify corresponding or similar elements throughout the several views, FIGS. 2A, 2B and 2C depict top views of a protective sterilization system in accordance with a preferred embodiment of the present application. It will be appreciated that system 201 overcomes one of more of the above-listed problems commonly associated with conventional sterilization systems.

In the contemplated embodiment, system 201 includes at least one implement 215 that is placed in a protective container 202 that is in turn sterilized in an autoclave 217.

The protective container 202 includes a first casing 203 that has a body 219 that encloses a storage space 221. The storage space 221 is closed by a second casing 205 that is configured to sever as a lid. The storage space 221 also has a plurality of support arms 207, 209, 211, 213 that are rigidly attached to the bottom surface 223 of storage space 221.

In use an implement 215 is placed on the support arms 207, 209, 211, 213. The space 221 is the closed by placing the second casing 205 on 203. The container 202 is then placed into the autoclave 217 and sterilized.

It should be appreciated that one of the unique features believed characteristic of the present application is that the implements 215 are individually supported and protected to prevent damage.

Another unique feature believed characteristic of the present application is that the casings 203, 205 reduce the exposure of the implements 215 to contamination after they have been sterilized.

Figure 3:
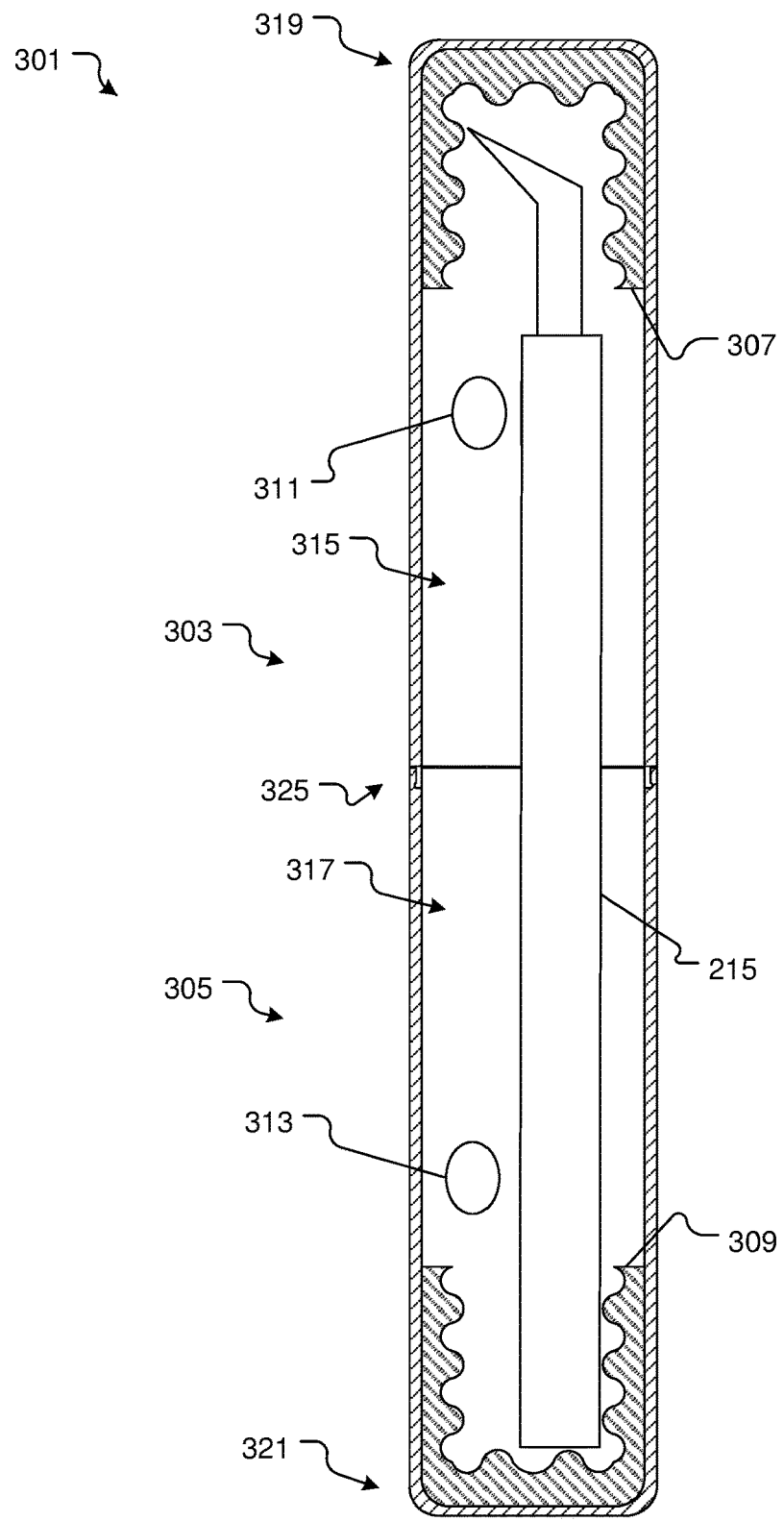
FIG. 3 is a cross-sectional top view of an alternative embodiment of the container of FIGS. 2A, 2B, and 2C.

FIG. 3 depicts an alternative embodiment of the protective container 202 of FIGS. 2A, 2B and 2C. In this embodiment the protective container 301 includes a plurality of casing halves 303, 305 that each enclose a storage space 315, 317 respectively when joined together via tongue and grooves 325.

Each halve 303, 305 have at least one hole 311, 313 respectively, that penetrates to the storage spaces 315, 317. Each halve 303, 305 having a support 307, 309 respectively, rigidly attached to the closed end 319, 321 of storage space 315, 317. It will be appreciated that the protective means 307, 309 could be rubber, silicone or any other material that prevents damage to the implements 215 placed in the casings 303, 305. It will be also appreciated that holes 311, 313 could be vents or any other form for allowing steam or any other sterilization means to come in contact with the implement 215.

Figure 4:
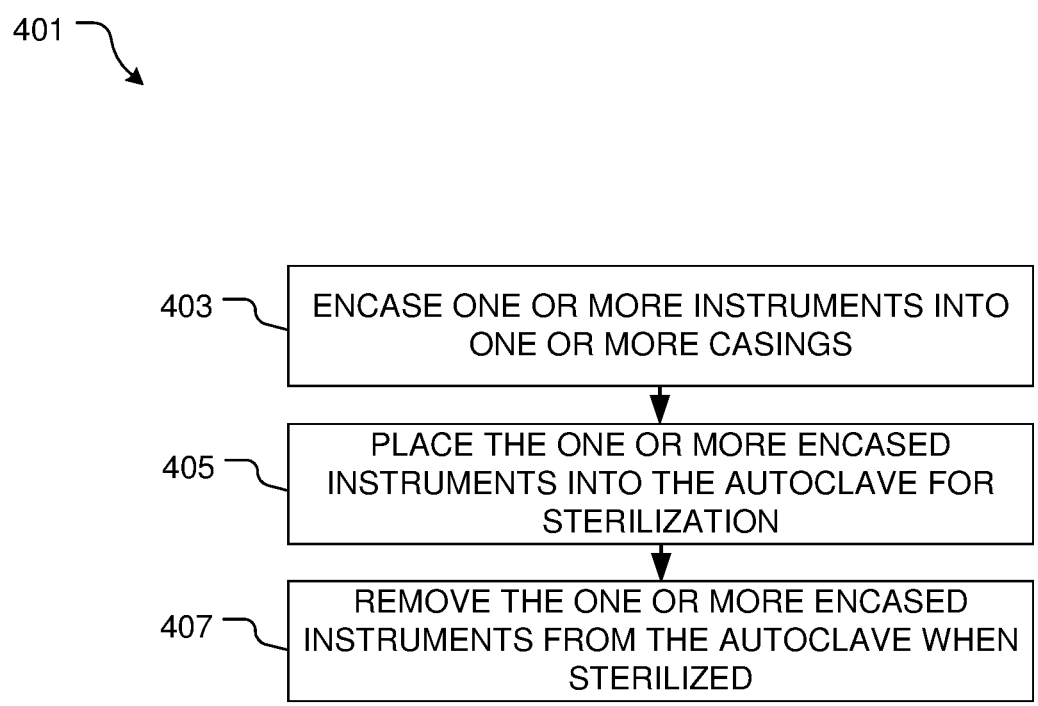
FIG. 4 is a flowchart of the process of the system of FIGS. 2A, 2B, and 2C.

FIG. 4 depicts a method of use of the system 201 of FIGS. 2A, 2B and 2C. The process 401 including encasing the one or more implements within the one or more casings 403, placing the one or more encased implements into the autoclave for sterilization 405, and removing the one or more encased implements from the autoclave when sterilized 407.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A protective sterilization system comprising:
a protective container, having:
   a first casing member having a body forming a storage space having:
      the body extending from a first enclosed end to a first open end, the first enclosed end having at least a first side, a second side, and a third side, the third side being opposite the first open end and extending between the first side and the second side;
      a bottom surface; and
      a first protection device positioned within the storage space at the first enclosed end of the body and attached to at least the first side, the second side, and the third side of the first enclosed end and extending inwardly into the storage space from at least the first side, the second side, and the third side of the first enclosed end;
   a plurality of support arms rigidly attached to the bottom surface of the storage space and configured to suspend an implement within the storage space of the container; and
   a second casing member having a second enclosed end and a second open end and configured to removably attach to the first casing member at the first open end of the first casing and the second open end of the second casing member via tongue and grooves, the second casing member having:
      a second protection device extending from the second enclosed end configured to hold the implement in a stationary position;
wherein the container when closed is sterilized to clean the implement.

2. The protective sterilization system of claim 1, further comprising:
a hole that penetrates a thickness of the first casing member to facilitate sterilization of the implement.

3. The system of claim 2 wherein the hole is a vent that can be opened and closed.

\* \* \* \* \*